United States Patent
Thomas, Jr.

[19]

[11] Patent Number: 6,110,173
[45] Date of Patent: Aug. 29, 2000

[54] TRANSVERSE CONNECTOR FOR SPINAL FIXATION SYSTEMS

[75] Inventor: James C. Thomas, Jr., Las Vegas, Nev.

[73] Assignee: Advanced Spine Fixation Systems, Inc., Irvine, Calif.

[21] Appl. No.: 09/153,315

[22] Filed: Sep. 15, 1998

[51] Int. Cl.[7] .................................................. A61B 17/56
[52] U.S. Cl. .............................................. 606/61; 606/72
[58] Field of Search ................................ 606/60, 61, 54, 606/55, 62–64

[56] References Cited

U.S. PATENT DOCUMENTS

| | | | |
|---|---|---|---|
| 5,074,864 | 12/1991 | Cozad et al. | 606/54 |
| 5,084,049 | 1/1992 | Asher et al. | 606/61 |
| 5,127,912 | 7/1992 | Ray et al. | 606/61 |
| 5,275,600 | 1/1994 | Allard et al. | 606/61 |
| 5,312,405 | 5/1994 | Korotko et al. | 606/61 |
| 5,330,473 | 7/1994 | Howland | 606/61 |
| 5,382,248 | 1/1995 | Jacobson et al. | 606/60 |
| 5,545,164 | 8/1996 | Howland | 606/61 |
| 5,601,554 | 2/1997 | Howland et al. | 606/61 |
| 5,630,816 | 5/1997 | Kambin | 606/61 |
| 5,688,272 | 11/1997 | Montague et al. | 606/61 |
| 5,716,355 | 2/1998 | Jackson et al. | 606/61 |
| 5,797,910 | 8/1998 | Martin | 606/61 |
| 5,947,966 | 9/1999 | Drewry et al. | 606/61 |

FOREIGN PATENT DOCUMENTS

| | | |
|---|---|---|
| 734 688 | 10/1996 | European Pat. Off. . |
| WO 95/31147 | 11/1995 | WIPO . |
| WO 97/31580 | 9/1997 | WIPO . |

OTHER PUBLICATIONS

Bridwell, et al., "Texas Scottish Rite Hospital (TSRH) Instrumentation System," *The Textbook of Spinal Surgery*, Volume One, 1991, p. 221.
Sofamore Danek, "Low Profile Crosslink® Plates," 1997, product description sheet (two sides).
Sofamore Danek, "Multi Axial Screw System," 1997, product description sheet (two sides).

*Primary Examiner*—Michael Buiz
*Assistant Examiner*—Jonathan D. Goldberg
*Attorney, Agent, or Firm*—Christie, Parker & Hale, LLP

[57] ABSTRACT

A transverse connector is provided that is useful for adding rigidity to a spinal fixation system employing a pair of generally parallel spine rods. The transverse connector includes a body portion with a longitudinal aperture for receiving a shaft of an adjusting arm such that the adjusting arm can slide into and out of the longitudinal aperture. The body and adjusting arm, while being in sliding engagement for adjustment of the length of the transverse connector, are secured to one another by a set screw threaded into a threaded aperture provided on the body portion. The threaded aperture is generally perpendicular to the longitudinal aperture so that the tip of the set screw will form an interference fit against the shaft of the adjusting arm. Each of the body and adjusting arm includes a clamping assembly consisting of a pair of clamp halves which cooperate to grip one of the spine rods. Each pair of clamp halves fastens to a different one of the spine rods. The clamp halves are pressed together to grip the spine rods using a pair of nuts.

18 Claims, 4 Drawing Sheets

TRANSVERSE CONNECTOR FOR SPINAL FIXATION SYSTEMS

FIELD OF THE INVENTION

This invention relates to an implantable spinal fixation device for the surgical treatment of spinal disorders. More specifically, it relates to a transverse connector to be placed between a pair of spine rods to add stability to the spine rods and reduce torsion.

BACKGROUND OF THE INVENTION

Various types of spinal column disorders are known and include scoliosis (abnormal lateral curvature of the spine), kyphosis (abnormal backward curvature of the spine), excess lordosis (abnormal forward curvature of the spine), spondylolisthesis (forward displacement of a lumbar vertebra) and other disorders, such as ruptured or slipped discs, broken or fractured vertebrae and the like. Patients who suffer from such conditions often experience extreme and debilitating pain. A technique known as spinal fixation uses surgical implants which mechanically immobilize areas of the spine assisting the eventual fusion of the treated vertebrae. Such techniques have been used effectively to treat the above-described conditions and, in most cases, to give the patient relief from pain.

One particular technique for spinal fixation includes the immobilization of the spine by the use of a pair of spine rods that run parallel to the spine on the left and right sides of the spinous process. According to the technique, bone screws are applied in the pedicles of the appropriate vertebrae or to the sacrum, to act as the anchor points for the spine rods. The bone screws are generally placed two per vertebra, one at each pedicle on either side of the spinous process. Clamp assemblies join the spine rods to the screws. The spine rods are generally custom-bent to achieve the desired curvature of the spinal column. Examples of such spinal fixation devices can be found in U.S. Pat. Nos. 4,653,481 and 5,030,220, which are incorporated herein by reference. According to another technique, rather than using bone screws, lamina hooks can be fastened to a spine rod to connect one or more rods to a vertebra for distraction or compression.

It has been found that when a pair of spine rods are fastened in parallel on either side of the spinous process, the assembly can be significantly strengthened by using at least one additional stiffening member known as a transverse connector to horizontally connect the pair of spine rods. A number of different transverse connectors are known. Ideally such transverse connectors should provide strength and control torsion.

Installation of a spinal fixation device entails a lengthy and complicated surgical procedure. Therefore, any simplification of the assembly procedure of a spinal fixation device will tend to reduce the complications associated with the procedure. For this reason, a transverse connector should be simple in installation.

SUMMARY OF THE INVENTION

A transverse connector for connecting left and right longitudinally implanted spine rods includes a body with a telescoping adjusting arm. The body includes a clamping assembly at one end for receiving the first spine rod. At its opposite end is an aperture extending longitudinally through the body. The longitudinal aperture receives a cylindrical shaft located on a first end of the telescoping adjusting arm. The second end of the adjusting arm includes a clamping assembly for receiving the second spine rod. The cylindrical shaft of the adjusting arm slides within the longitudinal aperture of the body such that the clamping assemblies of the body and adjusting arm can be telescoped toward or away from one another to achieve a custom fit for a broad range of assemblies in which the two parallel spine rods may be at different distances from one another.

The body further includes a threaded aperture which intersects the longitudinal aperture, preferably at a right angle. A set screw is threaded into the threaded aperture and used to lock the body and adjusting arm to one another such that the clamping mechanisms are at a given distance from one another.

The clamping assemblies provided on the body and adjusting arm each include two clamp halves. The first clamp half for the body and the first clamp half for the adjusting arm are integral to the body and adjusting arm, respectively. A channel is provided in each of the first clamp halves for receiving its respective spine rod. Each of the first clamp halves also includes an integral threaded post used for fastening the first clamp half to its respective mating second clamp half. Like each of the first clamp halves, each of the second clamp halves includes a channel for receiving the spine rod. Each second clamp half also includes an aperture through which the threaded post of its respective first clamp half extends. A nut threaded onto each of the threaded posts of the first clamp halves is used to press the mating clamp halves to one another to securely grip the spine rods.

DESCRIPTION OF THE DRAWINGS

Features, aspects and advantages of the invention will be more fully understood when considered with respect to the following detailed description, appended claims and accompanying drawings where:

DETAILED DESCRIPTION OF THE INVENTION

The present invention relates to a transverse connector for use in connecting a pair of generally parallel spine rods, the spine rods being part of a spinal fixation system useful for treating various spinal disorders. The spine rods may be of the type fastened to the patient's spine with either pedicle screws or lamina hooks. Transverse connectors are useful for providing additional lateral and torsional support to such a construct, greatly improving its strength and stability.

Figure 1:
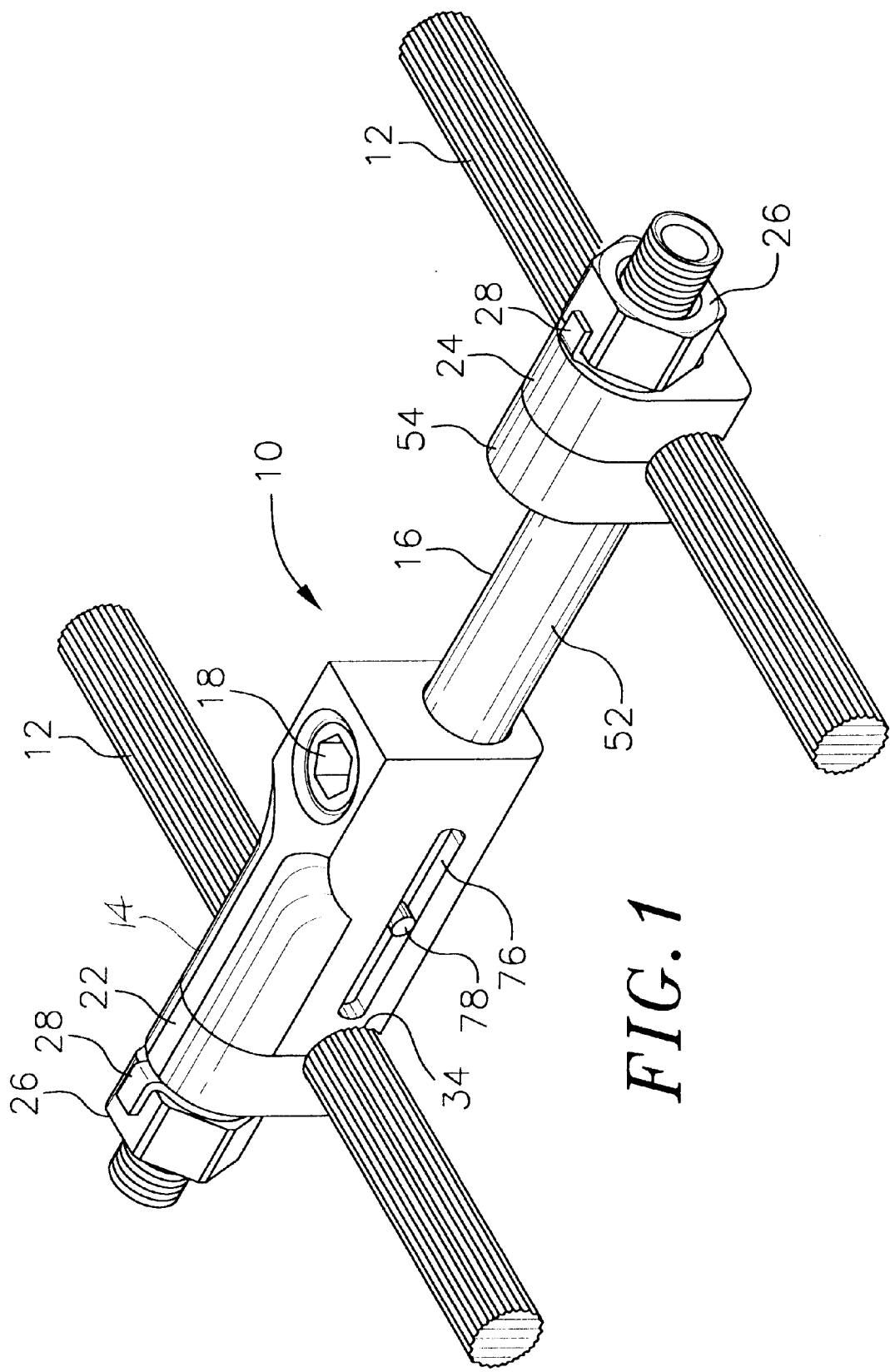
FIG. 1 is a perspective view of a transverse connector of the present invention assembled.
Figure 2:
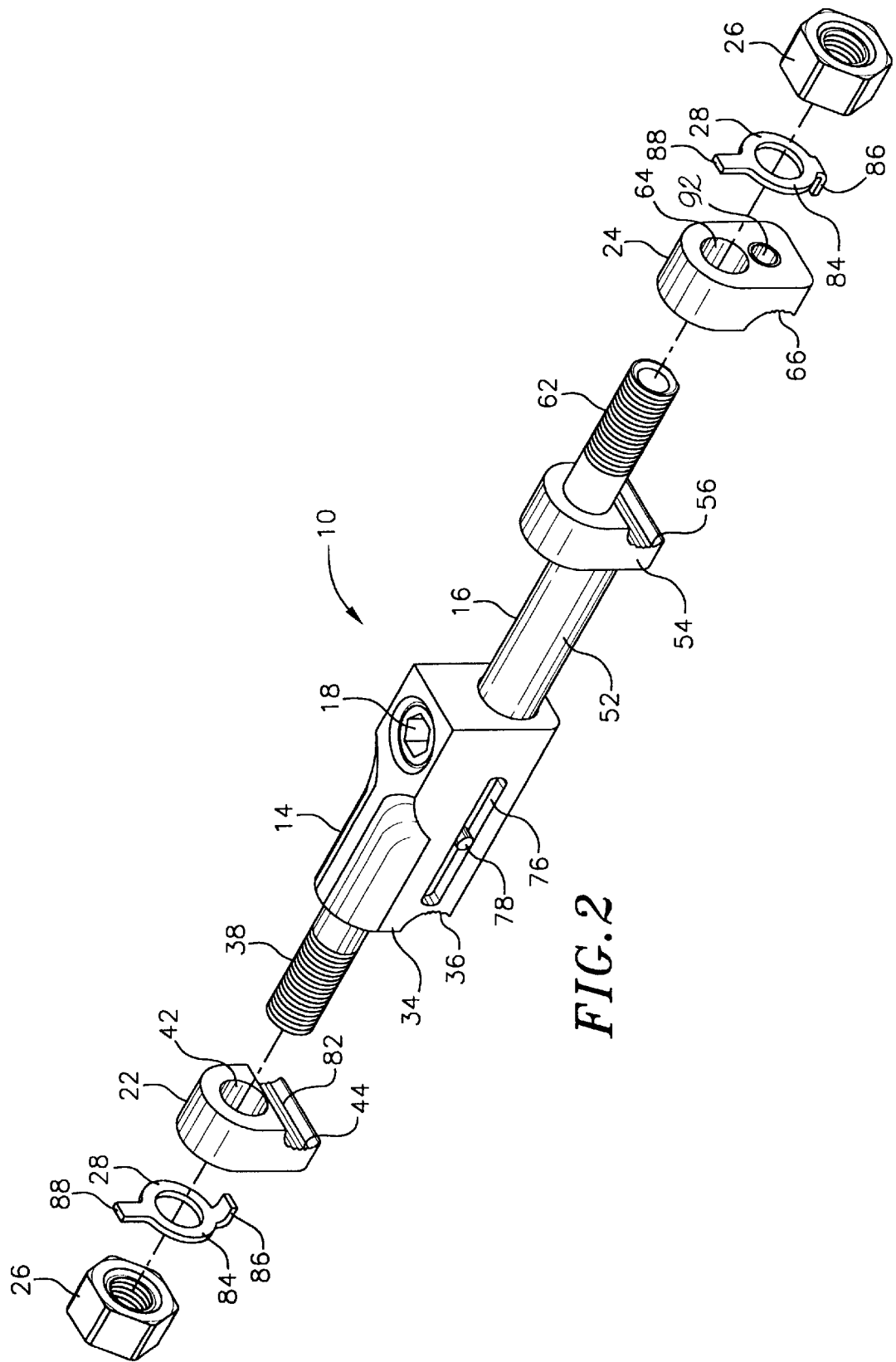
FIG. 2 is an exploded perspective view of the transverse connector of FIG. 1.
Figure 3:
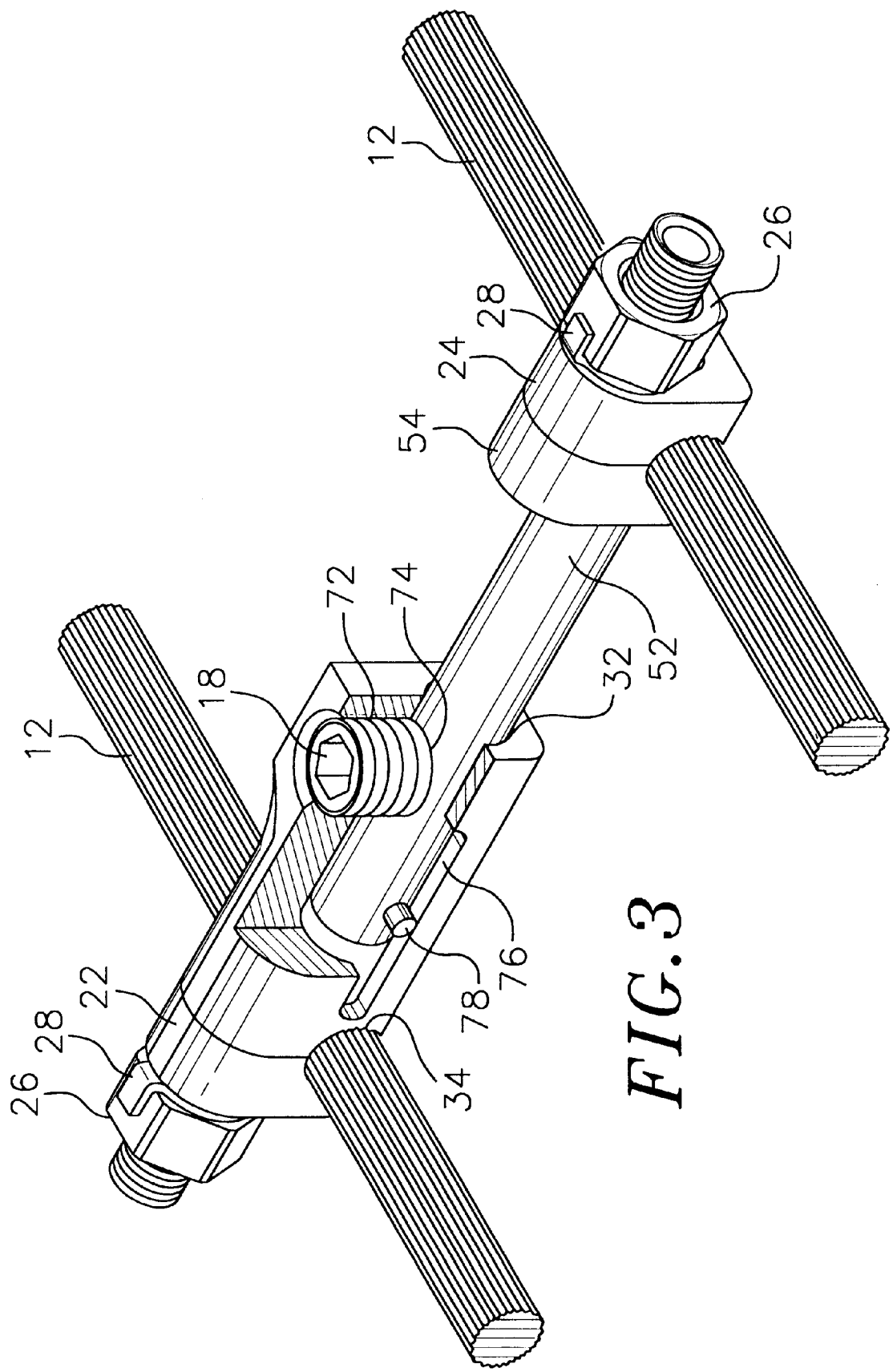
FIG. 3 is a perspective, partially cut away view of the device of FIG. 1.

Referring to FIG. 1–3, the general components of a transverse connector 10 according to the present invention are illustrated as attached to a pair of spine rods 12. The transverse connector includes a body 14 and an adjusting arm 16 that are adjustably attached to one another by a slide mechanism. Once properly adjusted, the body and adjusting arm are fixed to one another with a set screw 18. A pair of outer clamp halves 22, 24 are fastened to the body and adjusting arm with a pair of nuts 26. A pair of lock washers 28 are provided to hold the assembly together and prevent the nuts from loosening once the transverse connector is fastened to the pair of spine rods.

The details of the transverse connector are better illustrated in FIGS. 2–3. On one end, the body 14 includes a longitudinal cylindrical aperture 32. Opposite the longitudinal aperture and integral to the body is an inner clamp half 34 which includes an inner channel 36 for engaging the first spine rod. Extending from the inner clamp half in a direction generally parallel to the longitudinal aperture is a threaded post 38. Mounted on the threaded post is one of the two outer clamp halves 22. The first outer clamp half includes an aperture 42 through which the threaded post extends. The outer clamp half also includes a channel 44 for engaging the first spine rod. Together, the channels of the clamp halves extend around the spine rod to grip a significant surface area of the rod.

One of the two lock washers 28 fits over the threaded post and one of the two nuts 26 mates with the thread of the threaded post such that when tightened to the threaded post, the inner and outer clamp halves are drawn toward one another such that the inner and outer channels firmly grip the spine rod.

Turning to the adjusting arm 16, the adjusting arm is engaged with the body by a sliding shaft 52 which fits into the longitudinal aperture of the body. Opposite the shaft, the adjusting arm includes an inner clamp half 54 with an inner channel 56 for engaging the second spine rod. A threaded post 62 extends from the inner clamp in a direction generally parallel to the shaft. The second of the outer clamp halves 24 includes an aperture 64 through which the threaded post extends. An outer channel 66 is provided to engage the second spine rod. A nut 26 mates with the threaded post to draw the inner and outer clamps together to securely grip the second spine rod. As pointed out above, the clamp halves together grip a significant surface area of the spine rod to ensure a strong grip between the transverse connector and the spine rod. A lock washer 28 is provided to lock the assembly together once installed.

In order to lock the adjusting arm and body to one another and provide the desired rigidity to the assembly, the body also includes a threaded aperture 72 which intersects the longitudinal aperture. Preferably, the threaded aperture and longitudinal aperture are perpendicular to one another. The set screw 18 is inserted in the threaded aperture and a tip 74 engages the shaft of the adjusting arm to lock the two parts to one another.

In order to simplify the assembly, certain other features may be provided. Preferably, the body includes a longitudinal slot 76 which communicates with the longitudinal aperture. A pin 78 provided in the shaft of the adjusting arm and extending through the longitudinal slot of the body helps to hold the assembly together during installation. The pin slides along the length of the longitudinal slot to permit a full range of adjustment while holding the shaft within the longitudinal aperture. The pin also helps to prevent the adjusting arm from twisting with respect to the body. While the pin is illustrated as extending through a longitudinal slot provided on the side of the body, the longitudinal slot and pin could similarly be provided on the top or bottom of the body. The transverse connector is preferably preassembled by pre-drilling a hole for the pin and sliding the shaft of the adjusting arm into the longitudinal aperture of the body. Once the shaft is inserted into the longitudinal aperture, the hole of the shaft is aligned with the longitudinal slot of the body and the pin is pressed into place. An interference fit between the pin and hole of the adjusting arm will generally provide a sufficiently secure fit between the body and adjusting arm.

As another feature, the channels of the clamp halves preferably include a number of grooves 82 which help the channels to firmly grip the spine rods, especially if serrated spine rods are used. To further help lock the assembly in place, the nuts are locked to the body and adjusting arm, respectively, with lock washers, as set forth above. While any number of different lock washer designs may be provided, a preferred design is illustrated in the drawing figures. The lock washer includes a disc-shaped washer portion 84 from which extend first and second tabs 86, 88. The first tab is bent to be about perpendicular to the plane of the washer portion and extends into an aperture 92 provided on the outer side of the associated outer clamp half. Preferably, the first tab is pressed into place the aperture of the outer clamp half prior to installation of the transverse connector. An interference fit between the first tab and aperture assures that the lock washer stays in place. Once the transverse connector is installed to connect a pair of spine rods and the nuts have been securely tightened, the second tab can be bent to be about perpendicular with the plane of the washer portion to abut against one of the flat portions of the associated nut as is best shown in FIGS. 1–3. The second tab will prevent the nut from accidentally loosening once the transverse connector is installed. However, if the assembly needs to be removed and readjusted, the second tabs can be bent up to permit the nuts to be loosened.

As pointed out above, the transverse connector is preferably preassembled to some extent prior to its installation during surgery. The body and adjusting arm are preassembled with the pin holding the two together while permitting a full range of adjustability of the length of the connector. Similarly, the lock washers are press fit into place on the respective outer clamp halves. The outer clamp halves are also placed over the threaded posts prior to installation and the nuts are partially threaded into place. In the preferred embodiment, the outermost portion of each of the threaded posts is deformed after the nut is placed on the threaded post so as to prevent the nuts from backing off of the threaded posts prior to assembly. Because the device is preassembled, it is easier to install. Preassembly also reduces the risk that a part of the transverse connector might be dropped into the patient's body during the surgical procedure. It should be recognized that the threaded posts need to be sufficiently long to permit the inner and outer clamps to be spread far enough apart so that the transverse connector can easily be slid over the pair of spine rods without requiring the removal of the nuts.

For the preferred embodiment, all sharp edges for the various components are rounded so as to minimize irritation of the patient's muscle and other tissue once the device is installed. The transverse connector is best made of a strong metal such as stainless steel or titanium which is compatible with the human body. The transverse connector can also be anodized.

Figure 4:
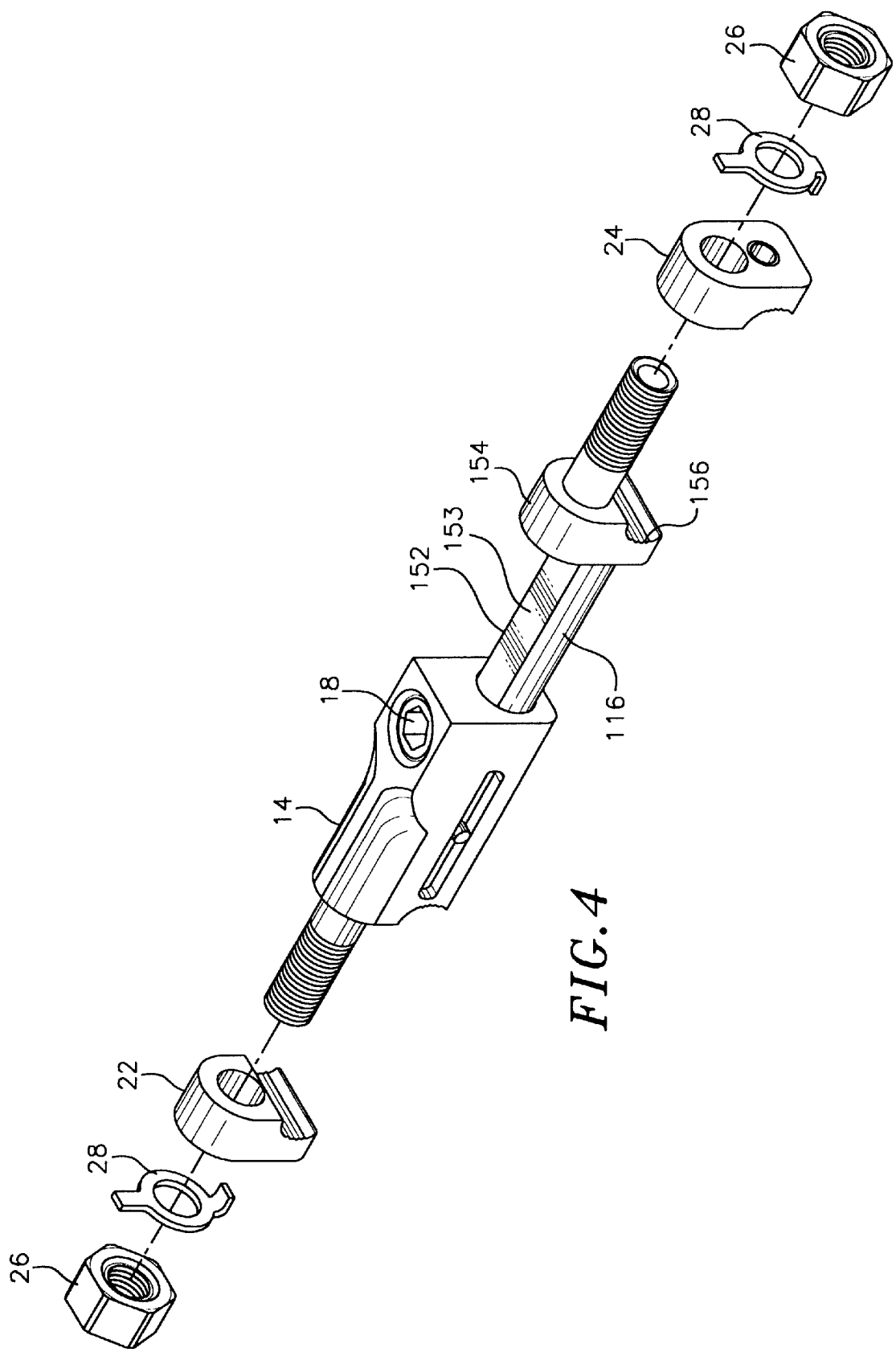
FIG. 4 is an exploded perspective view of an alternate embodiment of the invention.

Another embodiment of the invention is illustrated at FIG. 4. Here, the body 14, set screw 18, outer clamp halves 22, 24, nuts 26 and lock washers 28 are identical to the previous embodiment as are the various details of these specific components. The difference in this embodiment is that a modified adjusting arm 116 is provided in that the outer surface of the shaft 152 includes a flat top portion 153 rather than a continuous cylindrical surface. The adjusting arm includes an inner clamp half 154 which defines an inner channel 156 as discussed above. The benefit of this preferred design is that it can help to improve the grip between the set screw and the shaft of the adjusting arm. While not illustrated, when such a modified adjusting arm is provided, the longitudinal aperture of the body can also be provided with a flat top portion to mate with the modified adjusting arm. Similarly, the adjusting arm can be modified still further to include a shaft of a square, rectangular, triangular, or any other of a number of different shapes. For such shaped adjusting arms, the longitudinal aperture can be of similar geometric shape.

The installation of the transverse connector of the present invention is fairly straightforward. Prior to surgery, the transverse connector is preassembled as set forth above. The set screw is loosened so that the adjusting arm is freely adjustable with respect to the body. The nuts are also loosened so that the clamp halves will freely slip over the installed spine rods. Once the apparatus associated with the attachment of the spine rods to the patient's spine has been implanted, the transverse connector can be installed. First the half clamps of the transverse connector are slipped over the pair of spine rods at a point where the first and second spine rods are parallel with one another. The device is preferably located near the bottom of the overall construct, in the sacral or lumbar regions of the spine. Once the device is roughly placed in its proper location, the nuts are tightened to fasten the transverse connector securely to the spine rods. Once secured, the set screw is tightened to lock the adjusting arm and body to one another to provide the requisite rigidity. Once the location has been confirmed and the nuts and set screw have been securely tightened, the lock washers are bent to engage the nuts and prevent them from loosening. If multiple transverse connectors are to be used, then the steps above may be repeated. Because such a surgical procedure can take as long as six hours, an important benefit of the device of the present invention is the ease and simplicity of its installation.

Other variations of the transverse connector may include modifications in connecting the clamp halves to one another. For example, rather than including threaded posts integral to the body and adjusting arm for fastening the pairs of clamp halves to one another, bolts may be provided to extend through the apertures of the outer clamp halves and thread into threaded apertures provided in the inner clamp halves. Similarly, while in the preferred embodiment, the threaded posts are generally parallel to the shaft of the adjusting arm, the threaded posts may extend from the inner clamp halves at an angle from the adjusting arm.

Having described the preferred embodiments of the invention, the intended scope of the invention is defined by the following claims.

What is claimed is:

1. A cross link for joining together first and second spine rods spaced from one another a given distance, the cross link comprising:
   a body having first and second ends, the body defining a first clamp half on the first end and a longitudinal aperture that penetrates the second end;
   an adjusting arm having first and second ends, the first end adapted for sliding engagement with the longitudinal aperture of the body and the second end defining a second clamp half;
   a third clamp half;
   a first fastener comprising a first threaded post integral to the body and a first nut for engagement with the first threaded post to lock the first and third clamp halves to one another around the first spine rod to grip the first spine rod;
   a fourth clamp half;
   a second fastener comprising a second threaded post integral to the adjusting arm and a second nut for engagement with the second threaded post to lock the second and fourth clamp halves to one another around the second spine rod to grip the second spine rod; and
   a third fastener for locking the body and adjusting arm to one another to hold the first and second spine rods spaced from one another the given distance.

2. The cross link of claim 1 wherein the body further defines a slot and the adjusting arm further comprises a pin adapted for sliding engagement with the slot.

3. The cross link of claim 1 wherein the first and second posts are parallel to the longitudinal aperture of the body.

4. The cross link of claim 1 wherein the body further defines a threaded aperture intersecting with the longitudinal aperture and the first fastener comprises a set screw for engagement with the threaded aperture.

5. The cross link of claim 1 wherein each clamp half includes grooves.

6. A cross link for joining together first and second spine rods spaced from one another a given distance, the cross link comprising:
   a body having first and second ends, the body including a first clamp on the first end and a longitudinal aperture that penetrates the second end, the first clamp comprising:
      first and second clamp halves, each clamp half including a channel for receiving the first spine rod; and
      a first fastener comprising a first threaded post integral the body and a first nut, wherein the threaded post of the first fastener extends from the first clamp half and through the second clamp half to draw the first and second clamp halves together to grip the first spine rod;
   an adjusting arm having first and second ends, the first end adapted for sliding engagement with the longitudinal aperture of the body and the second end including a second clamp, the second clamp comprising:
      third and fourth clamp halves, each clamp half including a channel for receiving the second spine rod; and
      a second fastener comprising a second threaded post integral the adjusting arm and a second nut, wherein the threaded post extends from the third clamp half and through the fourth clamp half to draw the third and fourth clamp halves together to grip the second spine rod; and
   a third fastener for locking the body and adjusting arm to one another.

7. The cross link of claim 6 wherein the body further defines a slot and the adjusting arm further comprises a pin adapted for sliding engagement with the slot.

8. The cross link of claim 6 wherein the first and second posts are parallel to the longitudinal aperture of the body.

9. The cross link of claim 6 wherein the body further defines a threaded aperture intersecting with the longitudinal aperture and the first fastener comprises a set screw for engagement with the threaded aperture.

10. The cross link of claim 6 wherein each clamp half includes grooves.

11. A cross link for joining together first and second spine rods spaced from one another a given distance, the cross link comprising:
   a body having first and second ends, the body including a first clamp on the first end and a longitudinal aperture that penetrates the second end, the first clamp comprising:
      first and second clamp halves, each clamp half including a channel for receiving the first spine rod, wherein the first clamp half is integral to the body and further defines a first threaded aperture; and a first fastener adapted to draw the first and second clamp halves together to grip the first spine rod, wherein the first fastener comprises a first bolt extending through an aperture in the second clamp half and threaded into the first threaded aperture;

an adjusting arm having first and second ends, the first end adapted for sliding engagement with the longitudinal aperture of the body and the second end including a second clamp, the second clamp comprising:

third and fourth clamp halves, each clamp half including a channel for receiving the second spine rod wherein the third clamp half is integral to the adjusting arm and further defines a second threaded aperture; and a second fastener comprising a second bolt extending through an aperture in the fourth clamp half and threaded into the second threaded aperture to draw the third and fourth clamp halves together to grip the second spine rod; and a third fastener for locking the body and adjusting arm to one another.

12. The cross link of claim 11 wherein the body further defines a threaded aperture intersecting with the longitudinal aperture and the first fastener comprises a set screw for engagement with the threaded aperture.

13. The cross link of claim 11 wherein each clamp half includes grooves.

14. A cross link for joining together first and second spine rods spaced from one another a given distance, the cross link comprising:

a body having first and second ends, the body comprising:
a first clamp half integral to the first end;
a first post extending from the first clamp half;
a longitudinal aperture on the second end; and
a threaded aperture intersecting the longitudinal aperture;

an adjusting arm having first and second ends, the adjusting arm comprising:
a shaft integral to the first end adapted for sliding engagement with the longitudinal aperture of the body;
a second clamp half integral to the second end; and
a second post extending from the second clamp half;

third and fourth clamp halves, each including an aperture through which the first and second posts extend;

a first fastener for clamping the first and third clamp halves around the first spine rod;

a second fastener for clamping the second and fourth clamp halves around the second spine rod; and a set screw threaded into the threaded aperture.

15. The cross link of claim 14 wherein the first and second posts are threaded posts and the first and second fasteners are nuts.

16. The cross link of claim 14 wherein the first and second posts are parallel to the longitudinal aperture of the body.

17. The cross link of claim 14 wherein each clamp half includes a channel for gripping the spine rods.

18. The cross link of claim 14 wherein each clamp half includes grooves.

* * * * *